United States Patent [19]

Fanshawe et al.

[11] 4,302,589

[45] Nov. 24, 1981

[54] CIS-MONO AND DISUBSTITUTED-2-METHYL-3-[(PIPERAZINYL) AND (PIPERIDINO)ETHYL]INDOLINES, INTERMEDIATES FOR THEIR PREPARATION AND METHODS OF PREPARATION

[75] Inventors: William J. Fanshawe; Thomas C. McKenzie, both of Pearl River, N.Y.; Lantz S. Crawley, Clifton, N.J.

[73] Assignee: American Cyanamid Company, Stamford, Conn.

[21] Appl. No.: 147,806

[22] Filed: May 8, 1980

[51] Int. Cl.$^3$ .................. A61K 31/445; C07D 211/14
[52] U.S. Cl. .................... 546/201; 424/250; 424/263; 424/267; 544/360; 544/364; 544/373; 546/194; 546/193; 546/187; 260/326.13 B
[58] Field of Search ............... 544/364, 373; 546/201, 546/194

[56] References Cited

U.S. PATENT DOCUMENTS

| 3,183,235 | 5/1965 | Zenitz | 546/201 |
| 3,453,366 | 7/1969 | Mauvernay et al. | 544/373 |
| 3,466,287 | 9/1969 | Archer | 544/373 |
| 3,468,882 | 9/1969 | Laskowski | 544/373 |
| 3,751,416 | 8/1973 | Allen et al. | 544/373 |
| 3,751,417 | 8/1973 | Allen et al. | 544/373 |
| 4,089,853 | 5/1978 | Lanzilotti | 544/373 |

FOREIGN PATENT DOCUMENTS 1075156 7/1967 United Kingdom ............... 544/373

OTHER PUBLICATIONS

"Chemical Abstracts", vol. 60, 1964, col. 9293f to 9296b, (Abstract of British Patent No. 944,433, 12/11/63.
McKeon, "Chemical Abstracts", vol. 60, col. 18856(b).
Laskowski, "Chemical Abstracts", vol. 72, 1970, col. 43733v.
"Chemical Abstracts", vol. 77, 1972, col. 164758u, (Abstract of French Patent No. 2,102,282, 12/5/72).

Primary Examiner—Donald G. Daus
Assistant Examiner—James H. Turnipseed
Attorney, Agent, or Firm—Edward A. Conroy, Jr.

[57] ABSTRACT

Novel substituted 3-[2-(4-phenyl or pyridyl-1-piperazinyl or piperidino)ethyl]indolines useful as antipsychotic agents in mammals as well as substituted 3-[2-(4-phenylpiperidino)ethyl]indole intermediates for their preparation.

5 Claims, No Drawings

CIS-MONO AND DISUBSTITUTED-2-METHYL-3-[(PIPERAZINYL) AND (PIPERIDINO)ETHYL]INDOLINES, INTERMEDIATES FOR THEIR PREPARATION AND METHODS OF PREPARATION

DESCRIPTION OF THE INVENTION

This invention is concerned with new compounds of the formula:

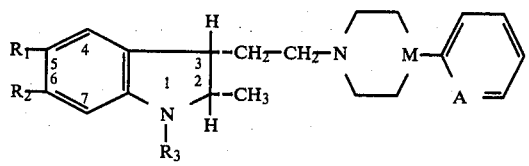

wherein $R_1$ is selected from the group comprising fluorine, chlorine, trifluoromethyl and methoxy; $R_2$ is hydrogen, chlorine and methoxy; $R_3$ is hydrogen and methyl and M and A may be carbon and nitrogen with the proviso that when A is nitrogen M must be nitrogen, and the pharmaceutically acceptable salts thereof.

This invention is also concerned with new compounds of the formula:

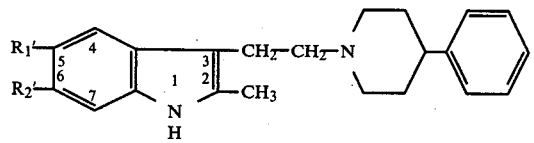

wherein $R'_1$ is selected from the group comprising fluorine and methoxy and $R'_2$ is hydrogen and methoxy and the pharmaceutically acceptable salts thereof; said compounds being useful as intermediates for the preparation of some of the antipsychotic indoline compounds described hereinabove. These intermediate indole compounds also possess activity as antipsychotic agents in mammals. The novel compounds of the present invention may be prepared as set forth in the following flow chart:

FLOWCHART

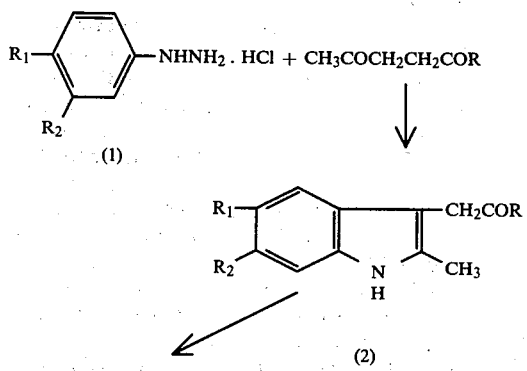

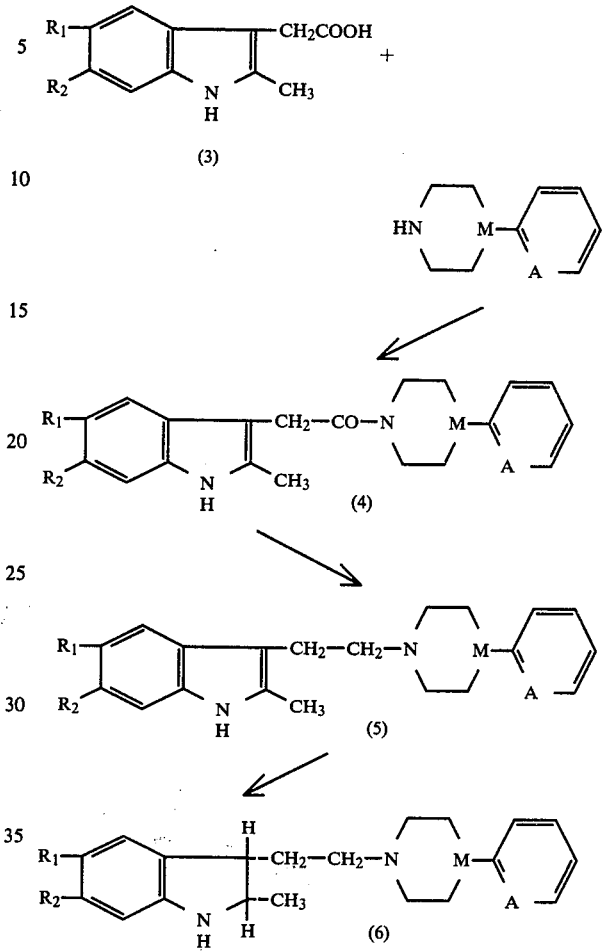

wherein R=OH and $OC_2H_5$; $R_1$=F, Cl, $CH_3O$ and $CF_3$; $R_2$=H, Cl, $CH_3O$ and M and A can be nitrogen or carbon with the proviso that when A is nitrogen M must be nitrogen.

A substituted phenylhydrazine hydrochloridde (1), such as 4-fluorophenylhydrazine hydrochloride, 3,4-dimethoxyphenylhydrazine hydrochloride or 3,4-dichlorophenylhydrazine hydrochloride is heated at reflux with levulinic acid or the ethyl ester therof in ethyl alcohol in the presence of concentrated sulfuric acid or hydrogen chloride gas for one hour to 6 days. The substituted-2-methyl-3-indoleacetic acid ethyl ester (2) is obtained by precipitation of the product with ice and water, followed by recrystallization of the product from a solvent mixture such as chloroform-hexane.

The substituted-2-methyl-3-indoleacetic acid (3) is obtained by heating the above ester (2) at reflux for 2–3 hours in aqueous sodium hydroxide. The aqueous solution is acidified, and extracted with ether, chloroform, or methylene chloride, or a mixture thereof. Evaporation of the extract provides the desired substituted-2-methyl-3-indoleacetic acid (3). The acid (3) is reacted for 1–16 hours with a compound such as N-phenylpiperazine, 4-phenylpiperidine, or N-(2-pyridyl)piperazine in tetrahydrofuran in the presence of N-methylmorpholine and isobutylchloroformate to give the desired 1-[(substituted-2-methyl-3-indolyl)acetyl]-4-phenyl or 4-(2-pyridyl)piperazine or 4-phenylpiperidine (4). The amide (4) is treated with a reducing agent such as sodium bis(2-methoxyethoxy)aluminum hydride or lithium aluminum hydride for 16-18 hours in a solvent such as benzene or tetrahydrofuran to provide the corresponding substituted-2-methyl-3-[2-(4-phenylpiperidino)ethyl]indole intermediate (5). The hydrochloride salt is obtained by treating an ethanol solution of the indole (5) with hydrogen chloride. The substituted 2-methyl-3-[2-(4-phenyl-1-piperazinyl)ethyl]indole and the (2-[4-(2-pyridyl)-1-piperazinyl]ethyl)indole intermediate compounds (5) are also obtained by the above procedures.

The intermediate indole compounds of this invention useful for the preparation of the novel indoline compounds of this invention, which may be prepared by the above methods, are for example:

5-fluoro-2-methyl-3-[2-(4-phenylpiperidino)ethyl]indole 5,6-dimethoxy-2-methyl-3-[2-(4-phenylpiperidino)ethyl]indole hydrochloride The appropriately substituted intermediate indoles (5) are dissolved in trifluoroacetic acid and are treated with triethylsilane at 45°-50° C. for 48-96 hours, or are heated at reflux in ethanol for 48 hours in the presence of tin and hydrochloric acid, and in each case the mixture is then poured onto cracked ice. The resultant mixtures are made basic and are extracted with solvents such as chloroform, methylene chloride, or ethyl acetate. The extracts are evaporated to give the substituted-2-methyl-3-[2-(4-phenylpiperidino), (4-phenyl-1-piperazinyl) and [4-(2pyridyl)-1-piperazinyl]ethyl]indoline compounds (6). The acid salts are obtained by treating the indoline (6) with hydrogen chloride in a solvent such as ethyl ether, ethyl acetate, or ethanol.

Typical compounds of the present invention which may be prepared by the above procedures are the following:

cis-5-fluoro-2-methyl-3-[2-(4-phenylpiperidino)ethyl]indoline dihydrochloride cis-5,6-dimethoxy-2-methyl-3-[2-(4-phenylpiperidino)ethyl]indoline dihydrochloride cis-5,6-dichloro-2-methyl-3-[2-(4-phenyl-1-piperazinyl)ethyl]indoline dihydrochloride cis-5,6-dimethoxy-2-methyl-3-2-[4-(2-pyridyl)-1-piperazinyl]ethyl indoline hydrochloride cis-5-fluoro-2-methyl-3-[2-(4-phenyl-1-piperazinyl)ethyl]indoline cis-5-fluoro-2-methyl-3-[2-(4-phenyl-1-piperazinyl)ethyl]indoline hydrochloride cis-5,6-dimethoxy-1,2-dimethyl-3-[2-(4-phenyl-1piperazinyl)ethyl]indoline cis-5,6-dimethoxy-1,2-dimethyl-3-[2-(4-phenyl-1-piperazinyl)ethyl]indoline fumarate cis-2-methyl-5-trifluoromethyl-3-[2-(4-phenyl-1-piperazinyl)ethyl]indoline dihydrochloride The novel compounds of the present invention show antipsychotic activity when administered to mammals as demonstrated by the antagonism of d-amphetamine lethality in grouped mice [see P. A. J. Janssen, et al., Arzneim-Forsch., 15, 104 (1965)].

Protection Versus d-Amphetamine Lethality in Grouped Mice

Known antipsychotics such as chlorpromazine and haloperidol protect grouped mice from the lethal effects of d-amphetamine sulfate. Other types of "tranquilizers" such as chlordiazepoxide and diazepam are ineffective.

Groups of 10 mice are treated orally or intraperitoneally with the test compounds at a dose of 20 mg./kg. of body weight. After an absorption time of 30 minutes for intraperitoneal administration and 60 minutes for oral administration, the mice are given intraperitoneal injections of d-amphetamine sulfate at a dose of 15 mg./kg. of body weight. The compounds are considered active if there is 50% or greater protection from lethality within 24 hours.

The results for the novel indoline compounds of this invention appear in Table I. The active novel indole intermediate compounds of the present invention are listed in Table II.

TABLE I

Grouped Amphetamine Lethality

| Compound | Result Method of Treatment | |
|---|---|---|
| | Oral | Intraperitoneal |
| cis-5-Fluoro-2-methyl-3-[2-(4-phenylpiperidino)ethyl]indoline dihydrochloride | | Active |
| cis-5,6-Dimethoxy-2-methyl-3-[2-(4-phenylpiperidino)ethyl]indoline dihydrochloride | Active | |
| cis-5,6-Dichloro-2-methyl-3-[2-(4-phenyl-1-piperazinyl)ethyl]indoline dihydrochloride | Active | |
| cis-5,6-Dimethoxy-2-methyl-3-{2-[4-(2-pyridyl)-1-piperazinyl]ethyl}indoline hydrochloride | | Active |
| cis-5-Fluoro-2-methyl-3-[2-(4-phenyl-1-piperazinyl)ethyl]indoline | Active | |
| cis-5,6-Dimethoxy-1,2-dimethyl-3-[2-(4-phenyl-1-piperazinyl)ethyl]indoline fumarate | Active | |

TABLE II

Grouped Amphetamine Lethality

| Compound | Result Method of Treatment | |
|---|---|---|
| | Oral | Intraperitoneal |
| 5-Fluoro-2-methyl-3-[2-(4-phenylpiperidino)ethyl]indole | | Active |
| 5,6-Dimethoxy-2-methyl-3-[2-(4-phenylpiperidino)ethyl]indole hydrochloride | Active | |

The present compounds, generally in the form of non-toxic salts, may be administered orally or parenterally and when so administered produce a therapeutically desirable effect on the central nervous system.

A wide range of doses may be employed ranging from about one to 100 mg., and a preferred range is from 2 to 25 mg. The dosage range is adjusted to provide an optimum therapeutic response in the warm-blooded animal being treated. hus, several doses may be administered daily, or the dose may be reduced proportionately as indicated by the exigencies of the therapeutic situation. The daily dosage range is from about 0.1 to about 10 mg./kg. with a preferred range, in many warm-blooded animals, of about 0.2 to about 5 mg./kg.

The active components of this invention can be used in compositions such as tablets; the principal active ingredient is mixed with conventional tableting ingredients, such as corn starch, lactose, sucrose, sorbitol, talc, stearic acid, magnesium stearate, dicalcium phosphate, gums or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating.

The liquid forms in which the novel compositions of the present invention may be incorporated for administration include suitably flavored emulsions with edible oils, such as cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification ofr the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

SPECIFIC DISCLOSURE

The following examples describe in detail the preparation of representative compounds of the present invention.

EXAMPLE 1

5-Fluoro-2-methyl-3-[2-(4-phenylpiperidino)ethyl]endole

A stirred mixture of 11.6 g. of levulinic acid, 16.3 g. of 4-fluorophenylhydrazine hydrochloride, 125 ml. of ethonal and 10 ml. of concentrated sulfuric acid is heated under reflux for 24 hours. The reaction mixture is poured onto cracked ice and water with formation of a precipitate. The light brown solid is collected, then is reprecipitated from chloroform with hexane to yield 12.0 g. of ethyl-5-fluoro-2-methyl-3-indoleacetate as light brown crystals.

A 7.2 g. portion of the preceding product is mixed with 25 ml. of water and 10 ml. of 10 N sodium hydroxide. The mixture is heated at reflux for 3 hours then is poured into water and made acidic with dilute aqueous hydrochloric acid. The mixture is extracted with ethyl ether. The ethereal extract is dried over magnesium sulfate and evaporated to provide light brown crystals. The material is recrystallized from acetonitrile to give 2.7 g. of 5-fluoro-2-methyl-3-indoleacetic acid as straw colored crystals.

To a cooled (dry ice-carbontetrachloride), stirred mixture of 8.4 g. of the preceding product, 4.5 g. of N-methylmorpholine and 200 ml. of tetrahydrofuran is added dropwise, under nitrogen, over a 10 minute period, 6.3 g. of isobutyl chloroformate in 40 ml. of tetrahydrofuran. Following this addition, 6.4 g. of 4-phenylpiperidine is added in small portions. The reaction mixture is allowed to warm to room temperature and is stirred 16 hours. The mixture is diluted with water and extracted with chloroform. The chloroform solution is dried and evaporated to give a tacky, orange glass. The glass is treated with hexane to provide cream-colored crystals. The crystalline material is dissolved in chloroform, then is washed with dilute aqueous hydrochloric acid and water. The chloroform solution is dried and the solvent is evaporated to give 10.5 g. of 1-[(5-fluoro-2-methyl-3-indolyl)acetyl]-4-phenyl piperidine as rusty pink crystals.

To a stirred mixture of 6.0 g. of the above product and 150 ml. of benzene is added dropwise, under nitrogen, over a 20 minute period at room temperature, 60 ml. of sodium bis-(2-methoxyethoxy)aluminum hydride. The reaction mixture is heated at reflux for 2 hours, then is allowed to stand 16 hours at room temperature. The reaction mixture is treated with 5 N sodium hydroxide to decompose the excess hydride, then is diluted with water. The benzene layer is separated and the aqueous phase is extracted with chloroform. The combined organic solutions are dried over magnesium sulfate and evaporated under reduced pressure to yield a tacky yellow solid. The solid is recrystallized from acetonitrile to give 1.2 g. of 5-fluoro-2-methyl-3-[2-(4-phenylpiperidino)ethyl]indole as cream-colored crystals, mp. 132°–134° C.

EXAMPLE 2 cis-5-Fluoro-2methyl-3-[2-(4-phenylpiperidino)ethyl]indoline dihydrochloride

A 1.9 g. amount of the product of Example 1 (prepared as described ) is dissolved in 50 ml. of trifluoroacetic acid. The solution is stirred and heated in an oil bath at a temperature of 50° C., then a 4.5 ml. volume of triethylsilane is added and the reaction mixture is stirred at 50° C. for 48 hours. The resulting solution is poured into a mixture of chopped ice and aqueous sodium hydroxide. This mixture is extracted with chloroform. The chloroform solution is dried over magnesium sulfate and concentrated to give a brown liquid. This liquid is mixed with dilute aqueous hydrochloric acid and is washed with ethyl ether. The aqueous phase is made basic with aqueous sodium hydroxide solution, then is extracted with chloroform. The chloroform extract is dried and concentrated to give 1.0 g. of a viscous brown liquid. The liquid is dissolved in ethyl acetate and is acidified with anhydrous hydrogen chloride to yield a precipitate of 0.8 g. of cis-5-fluoro-2-methyl-3-[2-(4-phenylpiperidino)ethyl]indoline dihydrochloride as a straw-colored solid, mp. 110°–125° C.

EXAMPLE 3

5,6-Dimethoxy-2methyl-3-[2-(4-phenylpiperidino)ethyl]indole hydrochloride

A 204 g. amount of 3,4-dimethoxyphenylhydrazine hydrochloride [J.C.S., 2061 (1949)] is suspended in a mixture of 2 liters of ethyl alcohol and 145 g. of ethyl levulinate under argon gas, then about 100 g. of hydrogen chloride gas is bubbled in and the mixture is refluxed for one hour and concentrated to a small volume. The concentrate is extracted with ethyl ether. the combined ether extract is washed with two 100 ml. portions of 2 N sodium hydroxide, water, and saturated aqueous sodium chloride solution. The ethereal solution is then filtered through a pad of magnesium silicate and evaporated to a dark oil. The oil is dissolved in two liters of water containing 1.5 moles of sodium hydroxide, then is heated at reflux for 2 hours. The solution is cooled, then is extracted with 500 ml. of ethyl ether. The aqueous layer is acidified with concentrated hydrochloric acid and filtered to yield 142.0 g. of 5,6-dimethoxy-2-methyl-3-indoleacetic acid as a tan powder.

To a cooled (dry ice-carbon tetrachloride) stirred mixture is 15.6 g. of the preceding product, 14.0 g. of N-methylmorpholine and 240 ml. of tetrahydrofuran is added dropwise, under nitrogen, over a 30 minute period, 10.0 g. of isobutyl chloroformate in 40 ml. of tetrahydrofuran. Following this addition, 10.3 g. of 4-phenylpiperidine is added and the reaction mixture is allowed to warm to room temperature and is stirred for 16 hours. The mixture is diluted with chloroform and water. The chloroform phase is separated and the aqueous phase is extracted with chloroform. The combined chloroform solution is washed with dilute hydrochloric acid, dried over magnesium sulfate and evaporated to yield a glassy brown tar. The tar is triturated with hexane to give a gray solid. The solid is dissolved in benzene, then hexane is added to precipitate 2.8 g. of 1-[(5,6-dimethoxy-2-methyl-3-indolyl)acetyl[-4-phenylpiperidine as a gray glass.

To a stirred mixture of 6.0 g. of the above product (prepared as described) and 150 ml. of benzene is added dropwise, under nitrogen, over a 15-minute period a room temperature, 60 ml. of sodium bis(2-methoxyethoxy)aluminum hydride. The clear solution is then heated at reflux for 2 hours, then stored for 16 hours at room temperature. The reaction mixture is treated with 5 N sodium hydroxide to decompose the excess hydride, then is siluted with water. The benzene layer is separated and the aqueous phase is extracted with chloroform. The combined organic extracts are dried over magnesium sulfate and evaporated under reduced pressure to yield a viscous brown liquid. The liquid is dissolved in absolute ethanol and is acidified with anhydrous hydrogen chloride, then ether is added to precipitate a solid. The solid is collected to give 4.6 g. of 5,6-dimethoxy-2-methyl-3-[2-(4-phenylpiperidino)ethyl]indole hydrochloride as gray crystals, mp. 152°–162° C. dec.

EXAMPLE 4 cis-5,6-Dimethoxy-2-methyl-3-[2-(4-phenylpiperidino)ethyl]indoline dihydrochloride A stirred mixture of 1.7 g. of the product of Example 3, 14.0 g. of mossy tin 35 ml. of ethanol and 28.0 ml. of concentrated hydrochloric acid is heated under reflux for 48 hours. The reaction mixture is poured into dilute aqueous sodium hydroxide. This mixture is filtered and the filter cake is extracted with ethyl acetate. The extract is dried over magnesium sulfate and the solvent is evaporated to give 1.12 g. of a brown tar. The tar is dissolved in ethyl acetate, then the solution is treated with anhydrous hydrogen chloride to make it just acidic. A solid is formed and is collected. The material is dissolved in isopropyl alcohol, then hexane is added to precipitate a solid. The mixture is dissolved in water, made basic with aqueous sodium hydroxide solution and extracted with chloroform. The chloroform is dried over magnesium sulfate and concentrated to give a viscous liquid. The liquid is dissolved in ethyl acetate. The solution is made just acidic with anhydrous hydrogen chloride to provide a precipitate. The precipitate is collected to give cis-5,6,-dimethoxy-2-methyl-3-[2-(4-phenylpiperidino)ethyl]indoline dihydrochloride as cream-colored crystals, mp. 125°–132° C.

EXAMPLE 5 cis-5,6,-Dichloro-2-methyl-3-[2-(4-phenyl-1-piperazinyl)ethyl]indoline dihydrochloride A stirred mixture of 46.4 g. of levulinic acid, 85.6 g. of 3,4-dichlorophenylhydrazine hydrochloride, 500 ml. of ethanol and 100 ml. of concentrated sulfuric acid is heated under reflux for 6 days. The reaction mixture is poured into chopped ice and water to form a precipitate. The precipitate is collected by filtration to provide a tacky brown solid. The solid is recrystallized from chloroform-hexane to yield 64.0 g. of a 50/50 mixture of ethyl-4,5(and 5,6)-dichloro-2-methyl-3-indoleacetate as light brown crystals. The entire amount of the above product is dissolved in 700 ml. of acetonitrile. The solution is then injected into a Waters Associates preparative liquid chromotography system using 30 ml. aliquots. The least polar fraction is collected and evaporated to give 29.5 g. of ethyl-5,6dichloro-2-methyl-3-indoleacetate as light brown crystals. A 26.0 g. portion of the preceding product is mixed with 200 ml. of water and 30 ml. of 10 N sodium hydroxide and heated under reflux for 3 hours. The reaction mixture is diluted with water and made acidic with dilute aqueous hydrochloric acid. A solid is precipitated and is extracted with ethyl ether, chloroform and methylene chloride. The organic extracts are combined, the solution is dried and concentrated. The crystals formed are collected to give 16.0 g. of 5,6-dichloro-2-methyl-3-indoleacetic acid as off-white crystals.

To a cooled (dry ice-carbon tetrachloride), stirred mixture of 2.6 g. of the preceding product, 1.2 g. of N-methyl morpholine and 50 ml. of tetrahydrofuran is added, dropwise, under nitrogen, over a 15 minute period, 1.9 g. of isobutylchloroformate in 25 ml. of tetrahydrofuran. Following this addition, 1.6 g. of N-phenylpiperazine in 20 ml. of tetrahydrofuran is added to the above mixture, dropwise, over a 10 minute period. The reaction mixture is allowed to warm to room temperature and is stirred for 16 hours. The mixture is diluted with water and extracted with chloroform. The chloroform extract is dried and evaporated to give a gummy, cream-colored solid. The solid is recrystallized from acetonitrile to yield 1.1 g. of 1-[(5,6-dichloro-2-methyl-3-indolyl)acetyl]-4-phenylpiperazine as cream colored crystals.

To a stirred mixture of 0.1 g. of lithium aluminum hydride in 50 ml. of dry tetrahydrofuran, at room termperature, under nitrogen, is added 0.4 g. of the above product. The reaction mixture is stirred for 16 hours, then the excess lithium aluminum hydride is decomposed by the addition of water saturated with sodium sulfate. Additional water is added, then the mixture is extracted with ethyl ether. The ethereal solution is dried and evaporated to give white crystals. The material is recrystallized from acetonitrile to yield 0.192 g. of 5,6-dichloro-2-methyl-3-[2-(4-phenyl-1-piperazinyl)ethyl]indole as white crystals.

To a stirred solution of 1.2 g. of the above product (prepared as described) and 30 ml. of trifluoroacetic acid warmed to an oil bath temperature of 45° C. is added 3.0 ml. of triethylsilane. The reaction mixture is then heated at 45°-50° C. for 96 hours. The reaction solution is then poured onto chopped ice and aqueous sodium hydroxide and the mixture is extracted with chloroform. The chloroform solution is extracted with aqueous hydrochloric acid, then the acid solution is made basic with 1-N sodium hydroxide and is extracted with chloroform with ethyl ether. The combined organic solution is dried and evaporated to give 0.4 g. of an oily film. The above material is dissolved in ethanolic-hydrogen chloride, then ethyl ether is added to precipitate a white solid. The solid is collected and dissolved in ethanol. The solvent is evaporated under reduced pressure to provide 0.2 g. of cis-5,6-dichloro-2-methyl-3-[2-(4-phenyl-1-piperazinyl)ethyl]indoline dihydrochloride as a straw-colored glass, mp. 140°-190° C. (dec.).

EXAMPLE 6 cis-5,6-Dimethoxy-2-methyl-3-{2-[4-(2-pyridyl)-1-piperazinyl]ethyl}indoline dihydrochloride To a cooled (dry ice-acetone), stirred mixture of 14.94 g. of 5,6-dimethoxy-2-methyl-3-indoleacetic acid (prepared in Example 2) and 6.6 g. of N-methylmorpholine in 240 ml. of dry tetrahydrofuran, is added dropwise 8.87 g. of isobutyl chloroformate in 40 ml. of dry tetrahydrofuran. Following this addition, 10.6 g. of 1-(2-pyridyl)piperazine is added in one portion and the reaction mixture is allowed to warm to room temperature, then is heated at 60° C. for one hour. The mixture is poured into 500 ml. of water, made strongly basic with aqueous sodium hydroxide and extracted 3 times with chloroform. The chloroform extracts are combined, copiously washed with water and dried over sodium sulfate. The solvent is evaporated to provide a dark gum. The gum is treated with ethyl ether to give a tan solid. This material is recrystallized from 400 ml. of hot ethanol after treatment with activated charcoal to yield 12.1 g. of 1-[(5,6-dimethoxy-2-methyl-3-indolyl)-acetyl]-4-(2-pyridyl)piperazine as a cream-colored solid.

To a stirred mixture of 6.0 g. of preceding product and 150 ml. of benzene is added 60 ml. of sodium bis(2-methoxyethoxy)aluminum hydride, dropwise, over a 15 minute period at room temperature under nitrogen. The resulting clear solution is heated at reflux for 2 hours, then is stirred at room temperature overnight. The excess hydride is decomposed with 5 N sodium hydroxide and the mixture is diluted with water. The mixture is extracted with chloroform. The chloroform solution is dried, then concentrated under reduced pressure to give a viscous liquid. The liquid is dissolved in ethanolic hydrogen chloride then ether is added to precipitate a solid. The solid is collected, then is mixed with water, made basic with sodium hydroxide and extracted with chloroform. The chloroform solution is dried, then is evaporated to give 2.5 g. of 5,6-dimethoxy-2-methyl-3-[2-[4-(2-pryidyl)-1-piperazinyl]ethyl]-indole as a gray glass.

The entire product above (2.5 g.) is dissolved in ethanol and acidified with ethanolic hydrogen chloride. The addition of ethyl ether produces a hygroscopic white precipitate which is collected by filtration. The material is allowed to stand and solidifies to yield 2.4 g. of 5,6-dimethoxy-2-methyl-3-[2-[4-(2-pyridyl)-1-piperazinyl]ethyl]indole dihydrochloride as a gray solid.

A 2.0 g. portion of the above product is dissolved in 50 ml. of trifluoroacetic acid and is stirred and heated to 50° C., then a 4.5 ml. portion of triethylsilane is added and the mixture is stirred and heated at 50° C. for 48 hours. The reaction mixture is poured onto chopped ice and aqueous sodium hydroxide. This mixture is extracted with chloroform. The chloroform solution is dried and concentrated to give a viscous brown liquid. The liquid is dissolved in ethyl acetate and acidified with anhydrous hydrogen chloride. The solid formed is collected by filtration to give 1.2 g. of a gray glass as the product of the Example, mp. 102°-110° C.

EXAMPLE 7 cis-5-Fluoro-2-methyl-3-[2-(4-phenyl-1-piperazinyl)ethyl]indoline

A 10.0 g. amount of 4-fluorophenylhydrazine hydrochloride is mixed with water and made basic with 5 N sodium hydroxide. The resulting mixture is extracted with ethyl ether. The ethereal solution is dried over anhydrous sodium sulfate and concentrated to give a black liquid. The liquid is dissolved in 50 ml. of ethanol, then a solution of 19.7 g. of 5-(4-phenyl-1-piperazinyl)-2-pentanone [C.A., 72, 43733V, pp. 470 (1970)] in 50 ml. of ethanol and 10 drops of glacial acetic acid is added and the solution is heated under reflux for 90 minutes. The clear solution is concentrated under reduced pressure to provide a viscous brown liquid. On standing, the liquid is partially solidified and the mixture is recrystallized from ethanol to give 6.4 of cream-colored crystals. A 1.0 g. portion of this material is recrystallized from ethanol to give 0.45 g. of 5-(4-phenyl-1-piperazinyl)-2-pentanone (p-fluorophenyl)hydrazone as white crystals.

A stirred 175 g. portion of polyphosphoric acid is heated to an oil bath temperature of 100° C., then 16.9 g. of the above product (prepared as described) is added in portions during a two minute period. The stirred mixture is heated at 100° C. for 5 minutes, then is poured into a mixture of cracked ice and concentrated ammonium hydroxide to give a brown solid precipitate. The precipitate is collected and is partially dissolved in 600 ml. of hot chloroform. The mixture is filtered and 700 ml. of hexane is added to the filtrate to precipitiate a light brown solid. The solid is removed by filtration and the filtrate is evaporated to give 7.6 g. of 5-fluoro-2-methyl-3-[2-(4-phenyl-1-piperazinyl)ethyl]indole as a brown tar which forms a hard brown glass on standing. The preceding product (7.6 g.) is dissovled in hot ethanol and diluted to 100 ml. with ethanol. A 50 ml. aliquot of the above solution is acidified with 1.5 ml. of concentrated hydrochloric acid, then an aqueous solution of 2.0 g. of sodium nitrate is added and the volume is adjusted to 100 ml. with water. A precipitate is formed and is collected by filtration to give 2.3 g. of 5-fluoro-2-methyl-3-[2-(4-phenyl-1-piperazinyl-ethyl]indole nitrate as light brown crystals.

A 2.9 g. amount of the above product (prepared as described) is mixed with 75 ml. of 5 N sodium hydroxide and is extracted with chloroform. The chloroform solution is dried over magnesium sulfate, then is concentrated to give 2.2 g. of a viscous brown liquid. The brown liquid is dissolved in 25 ml. of trifluoroacetic acid with stirring and heating at 50° C. in an oil bath. To this stirred solution is added 2.2 ml. of triethylsilane, the mixture is stirred and heated at 50° C. for 64 hours, then is poured into 25 ml. of water. A 50 ml. amount of chloroform is added and the mixture is made basic with aqueous potassium hydroxide. The chloroform layer is separated and the aqueous solution is extracted with additional chloroform. The chloroform solutions are combined, dried and concentrated to give 1.7 g. of a mixture of brown liquids. The above mixture is partially dissolved in dilute aqueous hydrochloric acid then is washed with ether and chloroform. The aqueous solution is made basic with 10 N sodium hydroxide and is extracted with chloroform. This chloroform solution is dried and concentrated to give 0.572 g. of cis-5-fluoro-2-methyl-3-[2-(4-phenyl-1-piperazinyl)ethyl]indoline as a yellow film.

EXAMPLE 8 cis-5-Fluoro-2-methyl-3-[2-(4-phenyl-1-piperazinyl)ethyl]indoline hydrochloride

A 0.3 g. portion of the product of Example 7 is dissolved in ethyl acetate and made slightly acidic with anhydrous hydrogen chloride. A solid is precipitated. The solid is collected and dried under reduced pressure to give 0.25 g. of light grey crystals identified as cis-5-fluoro-2-methyl-3-[2-(4-phenyl-1-piperazinyl)ethyl]indoline hydrochloride, mp. 230°–232° C. EXAMPLE 9 cis-5,6-Dimethoxy-1,2-dimethyl-3-[2-(4-phenyl-1-piperazinyl)ethyl]indoline

A 1.0 g. amount of cis-5,6-dimethoxy-2-methyl-3-[2-(4-phenyl-1-piperazinly)ethyl]indoline (U.S. Pat. Nos. 3,751,416 and 3,900,563) is dissolved in 25.0 ml. of 97% formic acid. The stirred solution is cooled to 15° C. in an ice-bath, then ten 10/32 inch pellets of sodium borohydride are added separately over a 15 minute period. The reaction mixture is allowed to stir 15 minutes longer, then is poured onto chopped ice and aqueous 10N sodium hydroxide. This mixture is extracted with methylene chloride. The organic solvent is dried and evaporated to yield a brown gum. The gum is distilled under reduced pressure on an Aldrich Kugelrohr apparatus at 250° C. and 0.025 mm. of mercury to provide 0.96 g. of the product of the Example as a yellow glass.

EXAMPLE 10 cis-5,6-Dimethoxy-1,2-dimethyl-3-[2-(4-phenyl-1-piperazinyl)ethyl]indoline furmarate The product of Example 9, 0.96 g., is dissolved in 5.0 ml. of hot ethanol and added to a hot solution of 0.57 g. of fumaric acid in 5.0 ml. of ethanol. The mixture is cooled to give a dark oil. The oil is triturated with isopropyl ether to give 1.03 g. of a brown glass. The product of the Example is obtained by twice dissolving the above material in ethanol, cooling and triturating with isopropyl ether, mp. 161° C. (dec.).

EXAMPLE 11 cis-5-Bromo-2-methyl-3-[2-(4-phenylpiperidino)ethyl]indoline

A stirred solution of 34.8 g. of levulinic acid, 66.9 g. of 4-bromophenylhydrazine hydrochloride, 400 ml. of ethanol and 30 ml. of concentrated sulfuric acid is heated under reflux for 24 hours. The reaction mixture is poured onto cracked ice and water forming an oily precipitate. The mixture is stored overnight at room temperature, then is filtered to collect 70.0 g. of a brown solid. The solid is recrystallized from ether-hexane to give 50.0 g. of light brown crystals. A 4.0 g. portion of the above material is recrystallized from chloroform-hexane to give 1.8 g. of ethyl-5-bromo-2-methyl-3-indoleacetate as light brown crystals.

A 25.0 g. amount of the preceding product (prepared as described) is mixed with 50 ml. of water and 15 ml. of 10 N sodium hydroxide and heated under reflux for 2 hours. The reaction mixture is diluted with water and made acidic with 6 N hydrochloric acid. The aqueous acid mixture is extracted with ethyl ether. The ethereal solution is dried and evaporated to give a light brown solid. The solid is recrystallized from acetonitrile to provide 9.3 g. of 5-bromo-2-methyl-3-indoleacetic acid as light brown crystals.

To a cooled (dry ice-carbon tetrachloride) stirred mixture of 10.8 g. of the above product (prepared as described), 4.5 g. of N-methylmorpholine and 200 ml. of tetrahydrofuran is added 6.3 g. of isobutylchloroformate in 40 ml. of tetrahydrofuran, dropwise over a 10 miute period, under nitrogen. Following this additin, 6.4 g. of 4-phenylpiperidine is added in small portions. The reaction mixture is allowed to warm to room temperature and is stirred overnight. The mixture is diluted with water and extracted with chloroform. The chloroform solution is dried and evaporated to give a light brown solid. The solid is recrystallized from chloroform-hexane to give 10.5 g. of 1-[(5-bromo-2-methyl-3-indolyl)acetyl]-4-phenylpiperidine as straw-colored crystals.

To a stirred mixture of 0.5 g. of lithium aluminum hydride in 200 ml. of dry tetrahydrofuran is added a solution of 2.0 g. of the preceding product in 40 ml. of tetrahydrofuran, dropwise, during a 10 minute period, under nitrogen and at room temperature. The reaction mixture is allowed to stir at room temperature for 48 hours.

Excess hydride is decomposed by the cautious addition of water saturated with sodium sulfate. The mixture is diluted with water and extracted with ethyl ether. The ethereal solution is dried and evaporated to give a tacky, straw-colored glass. The glass is recrystallized from acetonitrile to yield 1.2 g. of 5-bromo-2-methyl-3-[2-(4-phenylpiperidino)ethyl]indole as white crystals.

To a stirred solution of 2.5 g. of the above product in 60 ml. of trifluoroacetic acid warmed to an oil bath temperature of 45° C. is added, dropwise, 6.0 ml. of triethylsilane. The reaction mixture is stirred and heated at 45°–50° C. for 48 hours, then is poured onto cracked ice and aqueous sodium hydroxide. The mixture is extracted with chloroform. The chloroform extract is dried and concentrated to give a viscous liquid. The liquid is dissolved in ethanol and acidified with ethanolic hydrogen chloride, then ethyl ether is added to precipitate a solid. The solid is collected, mixed in water and is made basic with 10 N sodium hydroxide. The aqueous mixture is extracted with chloroform. The chloroform solution is dried and evaporated to give 1.7 g. of a gum. A 1.5 g. portion of the above material is dissolved in ethanol and acidified with ethanolic hydrogen chloride. The addition of ethyl ether precipitates a white solid. The solid is collected, dissolved in water, made basic with aqueous sodium hydroxide and extracted with chloroform. The chloroform extract is dried and evaporated to give 1.0 g. of a tacky white solid. The solid is recrystallized from acetonitrile to yield 0.6 g. of cis-5-bromo-2-methyl-3-[2-(4-phenylpiperidino)ethyl]indoline as white crystals, mp. 106°–108° C.

EXAMPLE 12

2-Methyl-5-trifluoromethyl-3-[2-(4-phenyl-1-piperazinyl)ethyl]indole

A stirred mixture of 11.6 g. of levulinic acid, 21.3 g. of 4-trifluoromethylphenylhydrazine hydrochloride, 125 ml. of ethanol and 10 ml. of concentrated sulfuric acid is heated under reflux for 24 hours. The reaction mixture is poured onto chopped ice and water. A precipitate forms and is collected by filtration to give ethyl-2-methyl-5-trifluoromethyl-3-indoleacetate.

A 25.0 g. amount of the preceding product (prepared as described) is mixed with 50 ml. of water and 15 ml. of 10 N sodium hydroxide and heated under reflux for 2 hours. The reation mixture is diluted with water and acidified with 6 N hydrochloric acid. The aqueous acidic mixture is extracted with ether. The ethereal solution is dried over magnesium sulfate and evaporated to give 2-methyl-5-trifluoromethyl-3-indoleacetic acid as the product.

To a cooled (dry ice-carbon tetrachloride), stirred mixture of 9.6 g. of the above product, 4.5 g. of N-methylmorpholine and 200 ml. of tetrahydrofuran is added 6.3 g. of isobutylchloroformate in 40 ml. of tetrahydrofuran dropwise, during 10 minutes, under nitrogen. Following this addition, 6.5 g. of 4-phenylpiperazine in 40 ml. of tetrahydrofuran is added dropwise. The reaction mixture is allowed to warm to room temperature and is stirred at room temperature for 16 hours. The reaction mixture is diluted with water and extracted with chloroform. The chloroform extract is dried over magnesium sulfate and concentrated under reduced pressure to give 1-[2-methyl-5-trifluoromethyl-3-indolyl)acetyl]-4-phenylpiperazine as the product.

To a stirred mixture of 1.0 g. of lithium aluminum hydride in 200 ml. of tetrahydrofuran is added a solution of 4.0 g. of the preceding product in tetrahydrofuran dropwise, over a 15 minute period, at room temperature under nitrogen. The mixture is stirred at room temperature for 16 hours, then the excess hydride is decomposed by the cautious addition of water, saturated with sodium sulfate. This mixture is diluted with water and extracted with ether. The ethereal solution is dried over magnesium sulfate and evaporated to give the product of the Example.

EXAMPLE 13 cis-2-Methyl-5-trifluoromethyl-3-[2-(4-phenyl-1-piperazinyl)ethyl]indoline dihydrochloride To a stirred solution of 1.2 g. of the product of Example 12 and 30 ml. of trifluoroacetic acid, heated to 50° C. is added 3.0 ml. of triethylsilane. This solution is stirred and heated at 50° C. for 96 hours. The reaction mixture is poured onto chopped ice and 50 ml. of 10 N sodium hydroxide. Then the aqueous mixture is extracted with chloroform. The chloroform solution is dried over magnesium sulfate and concentrated under reduced pressure to yield cis-2-methyl-5-trifluoromethyl-3-[2-(4-phenyl-1-piperazinyl)ethyl]indoline as the product. This compound is dissolved in ethyl acetate and acidified with anhydrous hydrogen chloride. The solid which precipitates is collected by filtration to provide the desired cis indoline dihydrochloride as the product of the Example.

We claim:

1. The compound cis-5-fluoro-2-methyl-3-[2-(4-phenylpiperidino)ethyl]indoline dihydrochloride.

2. The compound cis-5,-6-dimethoxy-2-methyl-3-[2-(4-phenylpiperidino)ethyl]indoline dihydrochloride.

3. A compound selected from those of the formula:

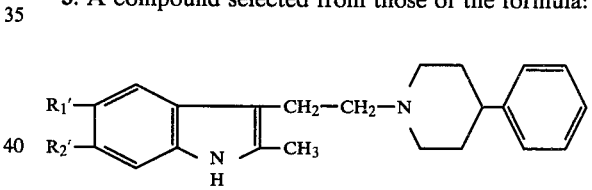

wherein $R'_1$ is selected from the group comprising fluorine and methoxy and $R'_2$ is hydrogen and methoxy, and the pharmacentically acceptable salts thereof.

4. The compound in accordance with claim 3, 5-fluoro-2-methyl-3-[2-(4-phenylpiperidino)ethyl]indole.

5. The compound in accordance with claim 3, 5,6-dimethoxy-2-methyl-2-[2-(4-phenylpiperidino)ethyl]indole hydrochloride.